US010379091B2

(12) United States Patent
Kraus et al.

(10) Patent No.: US 10,379,091 B2
(45) Date of Patent: Aug. 13, 2019

(54) AUTOMATIC TITRATOR

(71) Applicant: Ecolab USA Inc., St. Paul, MN (US)

(72) Inventors: Paul R. Kraus, Apple Valley, MN (US); Robert Ryther, Saint Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 190 days.

(21) Appl. No.: 15/511,730

(22) PCT Filed: Sep. 17, 2015

(86) PCT No.: PCT/US2015/050723
§ 371 (c)(1),
(2) Date: Mar. 16, 2017

(87) PCT Pub. No.: WO2016/044611
PCT Pub. Date: Mar. 24, 2016

(65) Prior Publication Data
US 2019/0033273 A1    Jan. 31, 2019

Related U.S. Application Data

(63) Continuation-in-part of application No. 14/489,215, filed on Sep. 17, 2014, now Pat. No. 9,766,183.

(51) Int. Cl.
G01N 31/16 (2006.01)
G01N 35/10 (2006.01)
G06F 17/11 (2006.01)
G16C 20/30 (2019.01)
G06F 16/22 (2019.01)

(52) U.S. Cl.
CPC ....... *G01N 31/166* (2013.01); *G01N 35/1002* (2013.01); *G06F 17/11* (2013.01); *G16C 20/30* (2019.02); *G06F 16/2237* (2019.01)

(58) Field of Classification Search
CPC .. G01N 31/166; G01N 31/16; G01N 35/1002; G01N 35/10; G01N 35/00; G06F 17/11; G06F 17/10; G06F 17/00
USPC .......................................................... 436/51
See application file for complete search history.

(56) References Cited

U.S. PATENT DOCUMENTS

| 5,192,509 | A | 3/1993 | Surjaatmadja et al. |
| 5,389,546 | A | 2/1995 | Becket |
| 6,010,664 | A | 1/2000 | Johnson et al. |
| 6,432,661 | B1 | 8/2002 | Heitfeld et al. |
| 7,153,695 | B2 | 12/2006 | Roeraade et al. |
| 7,349,760 | B2 * | 3/2008 | Wei ......... G01N 21/79 356/24 |
| 8,071,390 | B2 | 12/2011 | Tokhtuev et al. |
| 8,076,154 | B2 | 12/2011 | Erickson et al. |
| 8,076,155 | B2 | 12/2011 | Tokhtuev et al. |
| 8,119,412 | B2 | 2/2012 | Kraus |
| 8,143,070 | B2 | 3/2012 | Tokhtuev et al. |
| 8,178,352 | B2 | 5/2012 | Tokhtuev et al. |
| 8,236,573 | B2 | 8/2012 | Tokhtuev et al. |
| 8,980,636 | B2 | 3/2015 | Bolduc et al. |
| 2002/0151080 | A1 | 10/2002 | Dasgupta et al. |
| 2003/0032195 | A1 | 2/2003 | Roeraade et al. |
| 2003/0129254 | A1 | 7/2003 | Yasuhara et al. |
| 2006/0210961 | A1 | 9/2006 | Magnaldo et al. |
| 2006/0211129 | A1 * | 9/2006 | Stevens ......... G05D 11/138 436/173 |
| 2010/0136705 | A1 | 6/2010 | Kojima et al. |
| 2012/0028364 | A1 | 2/2012 | Kraus et al. |
| 2014/0273244 | A1 | 9/2014 | Bolduc et al. |

FOREIGN PATENT DOCUMENTS

JP    H06-58882 A    3/1994

OTHER PUBLICATIONS

Almeida et al, An automatic titrator based on a multicommunicated unsegmented flow system; Its application to acid-base titrations, Analytica Chimica Acta 407 (2000) 213-223.*
Sully, B. D., "The Analysis of Solutions of Per-Acids and Hydrogen Peroxide," Analyst, Aug. 1962, pp. 653-657, vol. 87.
Almeida, C. M. N. V., et al., "An Automatic Titrator Based on a Multicommutated Unsegmented Flow System Its Application to Acid-Base Titrations," Analytica Chimica Acta, 2000, pp. 213-223, vol. 407, No. 1.
Hetherington, M. A., et al., "A Novel PC-Based Gravimetric Autotitrator With a Multi-Solution Delivery System," Canadian Journal of Chemistry, 1995, pp. 1374-1379, vol. 73, No. 8.
Wojtowicz, M., et al., "Novel Approaches to Analysis by Flow Injection Gradient Titration," Analytica Chimica Acta, 2007, pp. 78-83, vol. 600, No. 1.

* cited by examiner

*Primary Examiner* — Christine T Mui
(74) *Attorney, Agent, or Firm* — Stinson LLP

(57) ABSTRACT

The present invention generally relates to continuous methods quantifying a target analyte concentration in a process solution. These methods are continuous automated titration methods that use titration chemistries to measure the target analyte concentration in the process solution. The method steps provide for efficient and robust automated titration methods for a variety of target analytes.

13 Claims, 9 Drawing Sheets

AUTOMATIC TITRATOR

CROSS-REFERENCE TO RELATED APPLICATION

This application claims priority to PCT Patent Application No. PCT/US2015/050723 filed on Sep. 17, 2015, which claims priority to U.S. patent application Ser. No. 14/489,215 filed on Sep. 17, 2014 (issued as U.S. Pat. No. 9,766,183), the disclosure of which is incorporated herein by reference in its entirety.

FIELD OF THE INVENTION

The present invention generally relates to continuous methods quantifying a target analyte concentration in a process solution. These methods are continuous automated titration methods that use titration chemistries to measure the target analyte concentration in the process solution. The method steps provide for efficient and robust automated titration methods for a variety of target analytes.

BACKGROUND OF THE INVENTION

Titration is a method well known and practiced to determine concentrations of components of a solution. Titrations of various chemistries are practiced, wherein generally a titrant is added to a solution in which it reacts with select components thereof. Once the entirety of the reacting component has reacted with the known titrant, a measureable or noticeable change occurs, indicating the reaction is complete. In some cases, the noticeable change comprises a color change. Color changes, for example, can vary widely across various chemistries of titrations.

While known as a science, titrations can be a tedious process, requiring careful practice by a chemist or other skilled operator. In some instances, it can be impractical to keep a chemist or other technician on hand to perform titrations, though data acquired by titrations can be desirable. Automated titrators can be implemented which attempt to judge when complete reactions have occurred and the appropriate titration calculations to determine an amount of a component in a solution. However, depending on the reaction, it can be difficult for an automated process to accurately determine an endpoint of a reaction. Additionally, automated systems can require a large amount of time to complete a process, which can be undesirable or unacceptable if a solution needs monitoring at certain time intervals.

SUMMARY OF THE INVENTION

One of the aspects of the invention is a continuous method for quantification of a target analyte concentration in a process solution. For example, a method for quantification of a target analyte concentration in a process solution comprising: continuously flowing the process solution through the analyzer; quantifying the target analyte concentration by changing the concentration of a titrant over a specified range; and detecting a titration endpoint for the reaction between the target analyte and a titrant within a specified target analyte concentration range.

Another aspect of the invention is a Go-No-Go continuous method for quantification of a target analyte concentration in a process solution. The method comprises (a) estimating the titrant concentration based on the estimated target analyte concentration, (b) introducing the titrant at a titrant flow rate calculated based on the estimated titrant concentration, (c) detecting the actual target analyte concentration or a concentration of a product produced by the reaction of the analyte and titrant, and (d) determining whether the actual target analyte concentration is greater than the estimated target analyte concentration, and if the actual target analyte concentration is greater than the estimated target analyte concentration then reporting the actual target analyte concentration.

Another aspect is the Go-No-Go method described herein wherein in step (d), if the actual target analyte concentration is less than the estimated target analyte concentration, the estimated target analyte concentration is decreased and steps (b), (c), and (d) are repeated with the lower estimated target analyte concentration until the actual target analyte concentration is greater than the estimated target analyte concentration.

Yet another aspect is a Window Analyte Concentration continuous method for quantification of a target analyte concentration in a process solution. The method comprises (a) determining a low estimated target analyte concentration and a high estimated target analyte concentration, (b) calculating a low flow rate of the titrant based on the low estimated target analyte concentration and a high flow rate of the titrant based on the high estimated target analyte concentration, (c) introducing the titrant at the low flow rate, (d) detecting the actual target analyte concentration, and (e) determining whether the actual target analyte concentration is greater than or equal to the low estimated target analyte concentration, and if the actual target analyte concentration is greater than or equal to the low estimated target analyte concentration then introducing the titrant at the high flow rate of the titrant, and determining whether the actual target analyte concentration is less than or equal to the high estimated target analyte concentration and if the actual target analyte concentration is less than or equal to the high estimated target analyte concentration then report the actual target analyte concentration is between the low estimated target analyte concentration and the high estimated target analyte concentration.

Yet a further aspect is the Window Analyte Concentration method described herein wherein step (e) comprises determining whether the actual target analyte concentration is greater than or equal to the low estimated target analyte concentration, and if the actual target analyte concentration is greater than or equal to the low estimated target analyte concentration then introducing the titrant at the high flow rate of the titrant, and determining whether the actual target analyte concentration is less than or equal to the high estimated target analyte concentration and if the actual target analyte concentration is not less than or equal to the high estimated target analyte concentration then reporting the actual target analyte concentration is greater than the high estimated target analyte concentration.

The Window Analyte Concentration method described herein can further comprise determining whether the actual target analyte concentration is greater than or equal to the low estimated target analyte concentration, and if the actual target analyte concentration is not greater than or equal to the low estimated target analyte concentration, then reporting that the actual target analyte concentration is less than the low estimated target analyte concentration.

A further aspect of the invention is a Binary Search Window continuous method for quantification of a target analyte concentration in a process solution. The method comprises (a) determining a first low estimated target analyte concentration and a first high estimated target analyte concentration, (b) determining a test precision value, (c)

calculating the first test range of the difference between the first high estimated target analyte and the first low estimated target analyte concentration, (d) determining whether the test precision value is greater than the first test range, and if the test precision value is greater than the first test range, then reporting the value.

Another aspect of the Binary Search Window method described herein wherein step (d) is as follows and further comprising steps (e)-(i); (d) determining whether the test precision value is greater than the first test range, and if the test precision value is not greater than the first test range, then calculating the first test range midpoint, (e) calculating a first midpoint flow rate of the titrant based on the first test range midpoint of the estimated target analyte concentration, (f) introducing the titrant at the first midpoint flow rate, (g) determining whether the endpoint of the reaction between the target analyte and the titrant can be detected, and if the endpoint can be detected, setting a second high estimated target analyte concentration to the first test range midpoint, (h) calculating the second test range of the difference between the second high estimated target analyte and the first low estimated target analyte concentration, and (i) determining whether the test precision value is greater than the second test range, and if the test precision value is greater than the second test range, then reporting the value.

Yet another aspect of the Binary Search Window method described herein wherein steps (g)-(i) are: (g) determining whether the endpoint of the reaction between the target analyte and the titrant can be detected, and if the endpoint cannot be detected, setting the second low estimated target analyte concentration to the first test range midpoint, (h) calculating the third test range of the difference between the second low estimated target analyte and the first low estimated target analyte concentration, and (i) determining whether the test precision value is greater than the third test range, and if the test precision value is greater than the third test range, then reporting the value.

Yet another aspect of the Binary Search Window method described herein wherein the steps of (g), (h), and (i) are repeated until the test precision value is greater than the new test range, then reporting the value.

Yet a further aspect is a kinetic continuous method for quantification of a target analyte concentration in a process solution. The method comprises (a) determining an estimated target analyte concentration, (b) calculating a first target analyte concentration range that is the difference between a first low estimated target analyte concentration and a first high estimated target analyte concentration, wherein the first low estimated target analyte concentration is calculated by subtracting a certain percentage value from the estimated target analyte concentration and the first high estimated target analyte concentration calculated by adding the same certain percentage value to the estimated target analyte concentration, (c) calculating a first low titrant flow rate based on the first low estimated target analyte concentration and calculating a first high titrant flow rate based on the first high estimated target analyte concentration, (d) introducing the titrant to the process solution at the first low titrant flow rate and gradually increasing the titrant flow rate to the first high titrant flow rate, and (e) determining whether the endpoint of the reaction between the target analyte and the titrant can be detected, and if the endpoint cannot be detected, increasing the first target analyte concentration range and repeating steps (c)-(e) until the endpoint can be detected.

Another aspect of the kinetic method described herein wherein step (e) is as follows and further comprises (e) determining whether the endpoint of the reaction between the target analyte and the titrant can be detected, and if the endpoint can be detected, calculating the first target analyte concentration midpoint and setting a second high estimated target analyte concentration to the first target analyte concentration midpoint, (f) calculating a second high flow rate based on the second high estimated target analyte concentration, (g) introducing the titrant to the process solution at the second high titrant flow rate and gradually decreasing the titrant flow rate to the first low titrant flow rate, and (h) determining whether the endpoint of the reaction between the target analyte and the titrant can be detected, and if the endpoint cannot be detected, increasing the first target analyte concentration range and repeating steps (c)-(e) until the endpoint can be detected.

Another aspect of the kinetic method described herein wherein step (h) is as follows and further comprises (h) determining whether the endpoint of the reaction between the target analyte and the titrant can be detected, and if the endpoint can be detected, (i) reporting the value and calculating the second target analyte concentration midpoint and setting a second low estimated target analyte concentration to the second target analyte concentration midpoint, calculating a second low flow rate based on the second low estimated target analyte concentration, and (j) introducing the titrant to the process solution at the second low titrant flow rate and gradually increasing the titrant flow rate until the flow rate is equal to the second high titrant flow rate.

Yet a further aspect of the invention is a dynamic window monitoring method for quantification of a target analyte concentration in a process solution comprising (a) inputting a low estimated target analyte concentration, a high estimated target analyte concentration, and a maximum integer value for a data counter, (b) setting the data counter to 1, (c) calculating a first target analyte concentration by dividing the sum of the low estimated target analyte concentration and the high estimated target analyte concentration by 2, (d) calculating a first target analyte flow rate based on the first target analyte concentration and introducing a titrant at the first target analyte flow rate, (e) measuring a first target analyte signal value that correlates to the actual target analyte concentration, (f) comparing the first target analyte signal value to a threshold target analyte signal value and a maximum target analyte signal value, and if the first target analyte signal value is between the threshold target analyte signal value and the maximum target analyte signal value, entering the first target analyte concentration and the first target analyte signal value as a first data pair into a data array, (g) if the data pair is entered into the data array, then increasing the data counter by 1, or if the data pair is not entered into the data array, repeating steps (c) to (f) with the data counter at the same value, (h) calculating a next target analyte concentration using the equation:

$$C_{l+1} = C_l + \frac{C_{max} - C_{min}}{n} \quad (1)$$

where n is the maximum integer value for the data counter, $C_{l+1}$ is the next target analyte concentration, $C_l$ is the previous target analyte concentration, $C_{max}$ is the high estimated target analyte concentration or the concentration calculated from equation 3 and $C_{min}$ is the low estimated target analyte concentration or the concentration calculated from equation 4, wherein if the next target analyte concentration, $C_{l+1}$, is greater than $C_{max}$, then $C_{l+1}$ is set to equal $C_{min}$, (i) calculating a next target analyte flow rate based on the next target analyte concentration and introducing a titrant at the next target analyte flow rate, (j) measuring a next target analyte signal value that correlates to the actual target analyte concentration, (k) comparing the next target analyte signal value to a threshold target analyte signal value and a maximum target analyte signal value, and if the next target analyte signal value is between the threshold target analyte signal value and the maximum target analyte signal value, entering the next target analyte concentration and the next target analyte signal value as a next data pair into the data array, (l) if the next data pair is entered into the data array, then increasing the data counter by 1, or if the next data pair is not entered into the data array, repeating steps (i) to (k) with the data counter set to the same value, (m) repeating steps (h)-(l) until the number of data pairs entered into the data array equals the maximum value for the data counter, (n) calculating $\Sigma x$, $\Sigma x^2$, $\Sigma y$, $\Sigma y^2$, and $\Sigma xy$ wherein x is the target analyte concentration and y is the signal value for each data pair, (o) calculating SXX, SYY, and SXY using the following equations:

$$SXX = \Sigma x^2 - \frac{(\Sigma x)^2}{n}, \quad (2a)$$

$$SYY = \Sigma y^2 - \frac{(\Sigma y)^2}{n}, \text{ and} \quad (2b)$$

$$SXY = \Sigma xy + \frac{(\Sigma x)(\Sigma y)}{n}, \quad (2c)$$

(p) calculating an endpoint concentration at (i) a minimum target analyte signal value when the target analyte concentration is inversely proportional to the target analyte signal value or (ii) a maximum target analyte signal value when the target analyte concentration is directly proportional to the target analyte signal value using the following equation:

$$C_{max} = \frac{\Sigma x}{n} - \left(\frac{SXX}{SXY}\right) \cdot \left(\frac{\Sigma y}{n}\right), \quad (3)$$

(q) calculating a minimum concentration at (i) a maximum target analyte signal value when the target analyte concentration is inversely proportional to the target analyte signal value or (ii) a minimum target analyte signal value when the target analyte concentration is directly proportional to the target analyte signal value using the following equation:

$$C_{min} = \left(\frac{SXX}{SXY}\right) \cdot \left(A_m - \frac{\Sigma y}{n} + \left(\frac{SXY}{SXX}\right) \cdot \frac{\Sigma x}{n}\right), \quad (4)$$

wherein $A_m$ is the target analyte signal value, (r) repeating steps (h)-(l) and reassigning the data pair designations so the first data pair entered is the first data pair replaced, (s) repeating steps (n)-(r) until the reaction endpoint is reached or the process is stopped.

DETAILED DESCRIPTION

Figure 1:
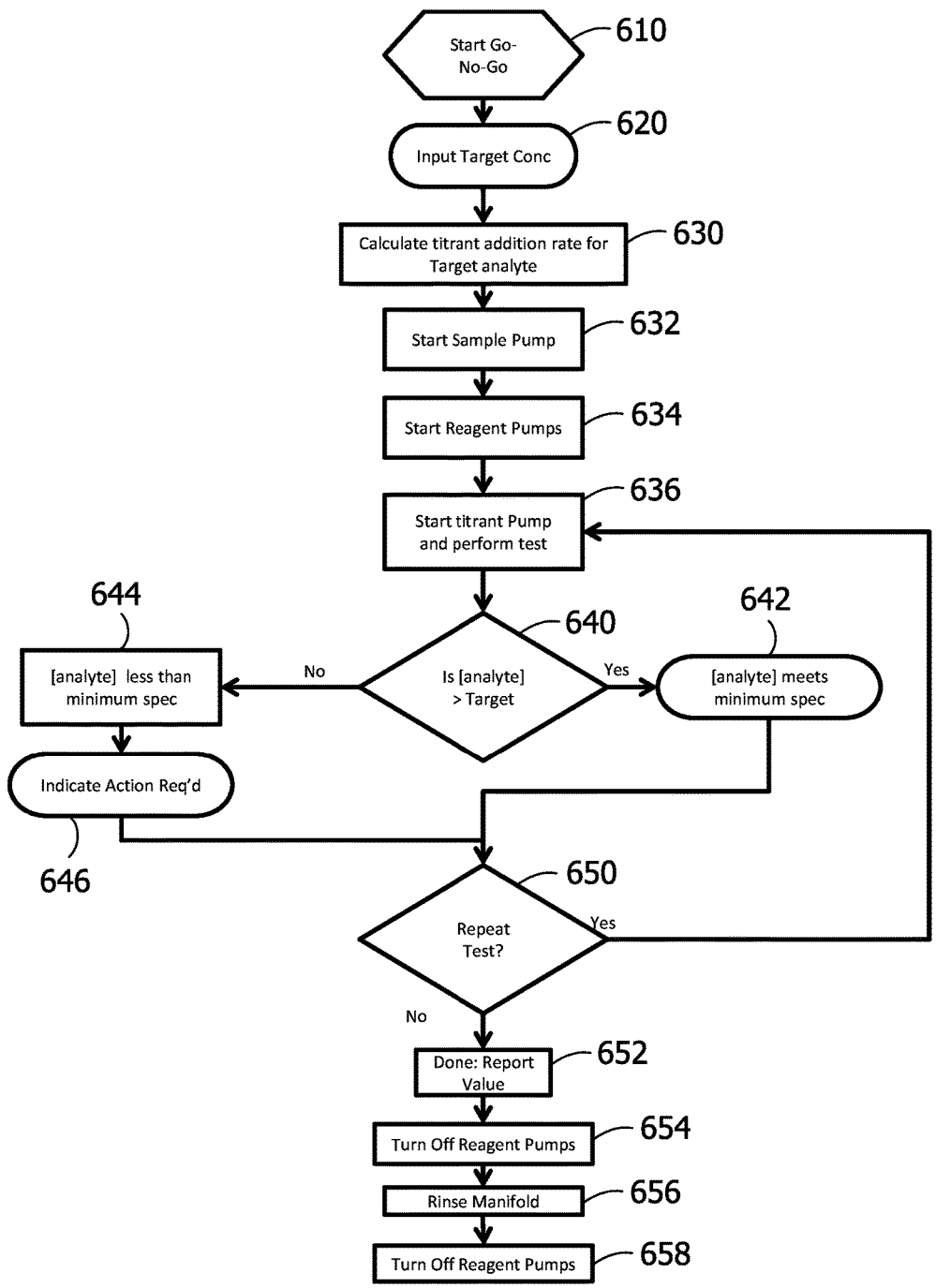
FIG. 1 is a process flow diagram for measuring whether a target analyte concentration is greater than a specified target analyte concentration.

The following description provides examples of the invention involving methods for determining amounts of target analytes in samples. The disclosure of methods directed to specific target analytes and titrants do not limit the scope of the invention in any way, but rather serve as examples to illustrate certain elements thereof. "Amount," as used herein, refers to a generic measureable quantity such as mass, concentration, volume, etc.

In a continuous mode of operation, a sample flows continuously and is analyzed without isolating any discrete portion of the sample. Instead, the sample flow rate is determined and/or controlled to be a known value.

One aspect of the invention is a method for quantification of a target analyte concentration in a process solution comprising: continuously flowing the process solution through the analyzer; quantifying the target analyte concentration by changing the concentration of a titrant over a specified range; and detecting a titration endpoint for the reaction between the target analyte and a titrant within a specified target analyte concentration range.

The methods described herein further comprising continuously adding a conditioning reagent to the process solution in a concentration proportional to the target analyte concentration.

The titration endpoint can be detected using a detector that is a defined distance from a point of titrant addition and calculating the titrant concentration using the distance between the detector and the point of titrant addition, the flow rate of the titrant, and the system volume.

Preferably, using the methods of the invention, the process solution is continuously refreshed.

The methods described herein can further comprise varying the titrant concentration by controlling its flow rate wherein the detector signal from the reaction product of the titration is correlated in time with the titrant concentration.

The methods described herein can also further comprise dosing a calibrant of known concentration into the process solution, detecting the calibrant concentration, and calculating the response.

The methods of quantification of a target analyte can further comprise varying the titrant concentration using a mathematical function and identifying the titration endpoint within the specific target analyte concentration range.

The mathematical function can be a linear function, a step-wise function, a sine function, a square wave function, an exponential function, or a combination thereof. The mathematical function can also be a linear function, a step-wise function, a sine function, a square wave function, or a combination thereof.

The methods can also further comprise controlling the titrant concentration using a feedback loop that responds to a detector detecting the reaction between the titrant and the target analyte.

The methods additionally can further comprise measuring the titration endpoint using a stepwise titrant concentration change over the specified target analyte concentration range.

The stepwise titrant concentration change can be a larger concentration change per step at the beginning of the reaction of the target analyte with the titrant and decreases to a smaller concentration change per step as the reaction proceeds towards the endpoint. An example of this process is described in Example 1 and shown in FIG. 8.

The methods described herein can also comprise the conditioning reagent treating the process solution to improve detection of the target analyte.

The methods described herein wherein the detection of the target analyte is improved by improving the sensitivity of the detection method.

The conditioning reagent can be a pH buffer, a reaction catalyst, a chemical indicator, a sequestrant, a surfactant, a conductivity modifying salt, an ion pair reagent, a biologically based chemical, or a combination thereof.

The variety of reagents that can be the conditioning reagent are well known to a person of ordinary skill in the art and can be applied to a wide variety of titration systems.

The titration endpoint can be detected using a light-based, electrochemically-based, or biologically-based detector.

The titration endpoint can be signaled by a detectable change at a complete reaction of the target analyte with the titrant. The detectable change can be a spectrophotometric change, an electrochemical change, or a pH change.

FIG. 1 is a process flow diagram of a Go-No-Go method for quantification of a target analyte concentration in a process solution wherein the PLC is started 610 and the method further comprises estimating the titrant concentration based on the estimated target analyte concentration and inputting the estimated target concentration into the PLC 620. Then, calculating the titrant flow rate based on the estimated analyte concentration 630, and starting the sample pump 632 and the reagent pumps 634. The titrant pump is started 636 and the test is performed 636. The actual target analyte concentration or a concentration of a product produced by the reaction of the analyte and titrant in the presence of the conditioning reagent is detected, and it is determined whether the actual target analyte concentration is greater than the estimated target analyte concentration 640. If the actual target analyte concentration is greater than the estimated target analyte concentration, then the target analyte concentration meets minimum specification 642 and the actual target analyte concentration is reported 652 as long as the test is not repeated 650. After the actual target analyte concentration is reported 652, the reagent pumps are turned off 654, 658, and the manifold is rinsed 656.

FIG. 1 further describes the process wherein if the actual target analyte concentration is not greater than the estimated target analyte concentration 640, the estimated target analyte concentration is less than the minimum specification 644, an appropriate action is indicated 646, and a lower value for the target analyte concentration is input 620 and the titration 636, concentration comparison 640 steps are repeated until the actual target analyte concentration is greater than the estimated target analyte concentration.

Figure 2:
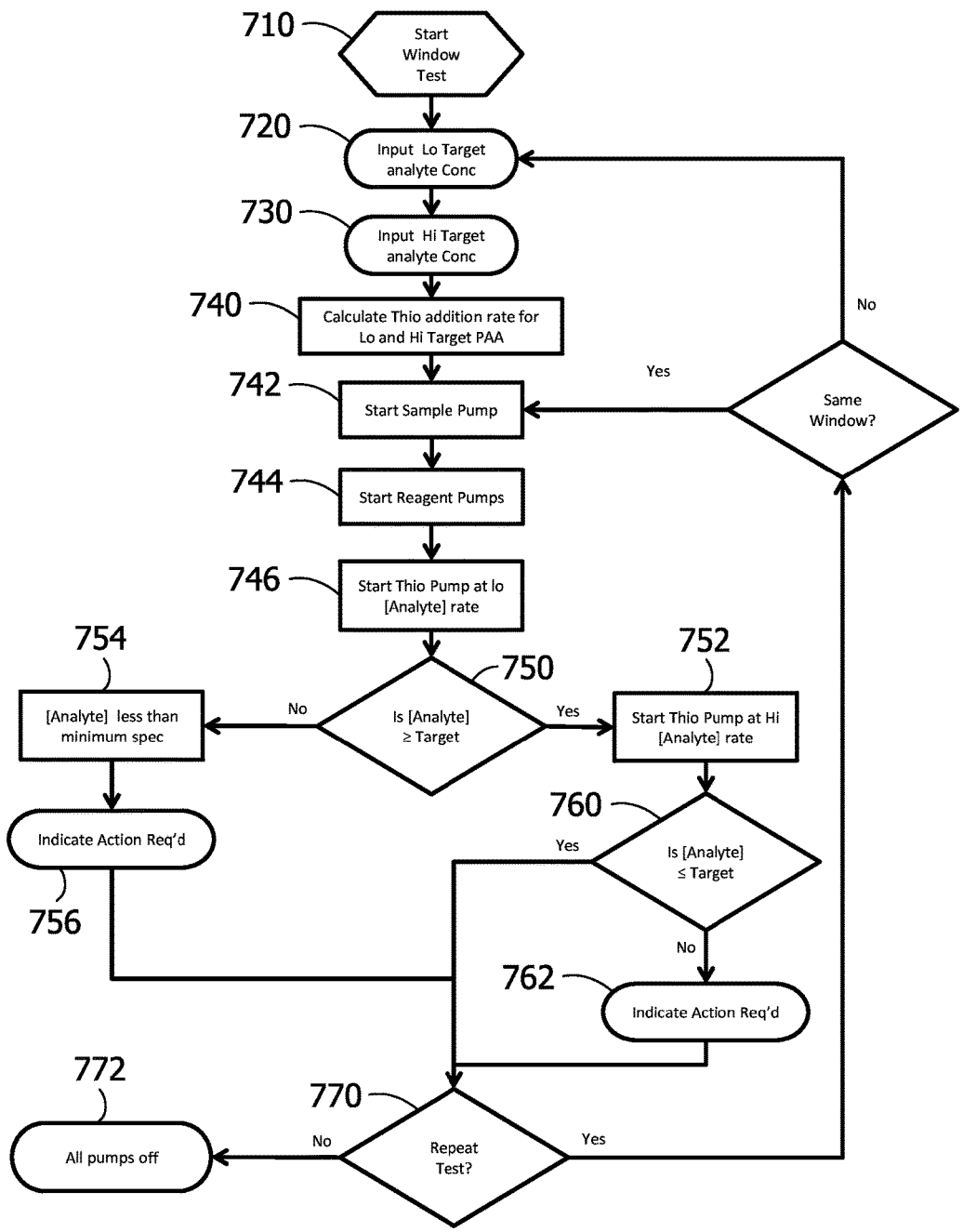
FIG. 2 is a process flow diagram for measuring whether a target analyte concentration is within a specified concentration range.

FIG. 2 is a process flow diagram of a Window Analyte Concentration method for quantification of a target analyte concentration in a process solution wherein the PLC is started 710, a low estimated target analyte concentration and a high estimated target analyte concentration are determined, the low estimated target analyte concentration is input into the PLC 720, and the high estimated target analyte concentration is input into the PLC 730. A low flow rate of the titrant based on the low estimated target analyte concentration and a high flow rate of the titrant based on the high estimated target analyte concentration are calculated 740, the sample pump is started 742, and the reagent pump is started 744. The titrant pump is started at the low flow rate of the titrant based on the low estimated target analyte concentration 746. The actual target analyte concentration is detected or calculated from detection of the concentration of a product produced by the reaction of the analyte and titrant in the presence of the conditioning reagent, and determining whether the actual target analyte concentration is greater than or equal to the low estimated target analyte concentration 750. If the actual target analyte concentration is greater than or equal to the low estimated target analyte concentration, then introducing the titrant at the high flow rate of the titrant 752, and determining whether the actual target analyte concentration is less than or equal to the high estimated target analyte concentration 760. If the actual target analyte concentration is less than or equal to the high estimated target analyte concentration then report the actual target analyte concentration is between the low estimated target analyte concentration and the high estimated target analyte concentration and turn of all pumps 772.

FIG. 2 further describes the process wherein if the actual target analyte concentration is greater than or equal to the low estimated target analyte concentration 750, then introducing the titrant at the high flow rate of the titrant 752, and determining whether the actual target analyte concentration is less than or equal to the high estimated target analyte concentration 760. If the actual target analyte concentration is not less than or equal to the high estimated target analyte concentration then indicating the action required 762, e.g., reporting the actual target analyte concentration is greater than the high estimated target analyte concentration.

FIG. 2 also describes the process of determining whether the actual target analyte concentration is greater than or equal to the low estimated target analyte concentration 750, and if the actual target analyte concentration is not greater than or equal to the low estimated target analyte concentration, the actual target analyte concentration is less than the minimum specification 754, and reporting that the actual target analyte concentration is less than the low estimated target analyte concentration 756.

FIG. 2 further comprises the option to repeat the test 770 and if the test is repeated, the option to use the same low estimated target analyte concentration and the same high estimated target analyte concentration. Alternatively, the operator can choose to use a different low estimated target analyte concentration and a different high estimated target analyte concentration. If the test is not repeated, all pumps are turned off 772.

Figure 3:
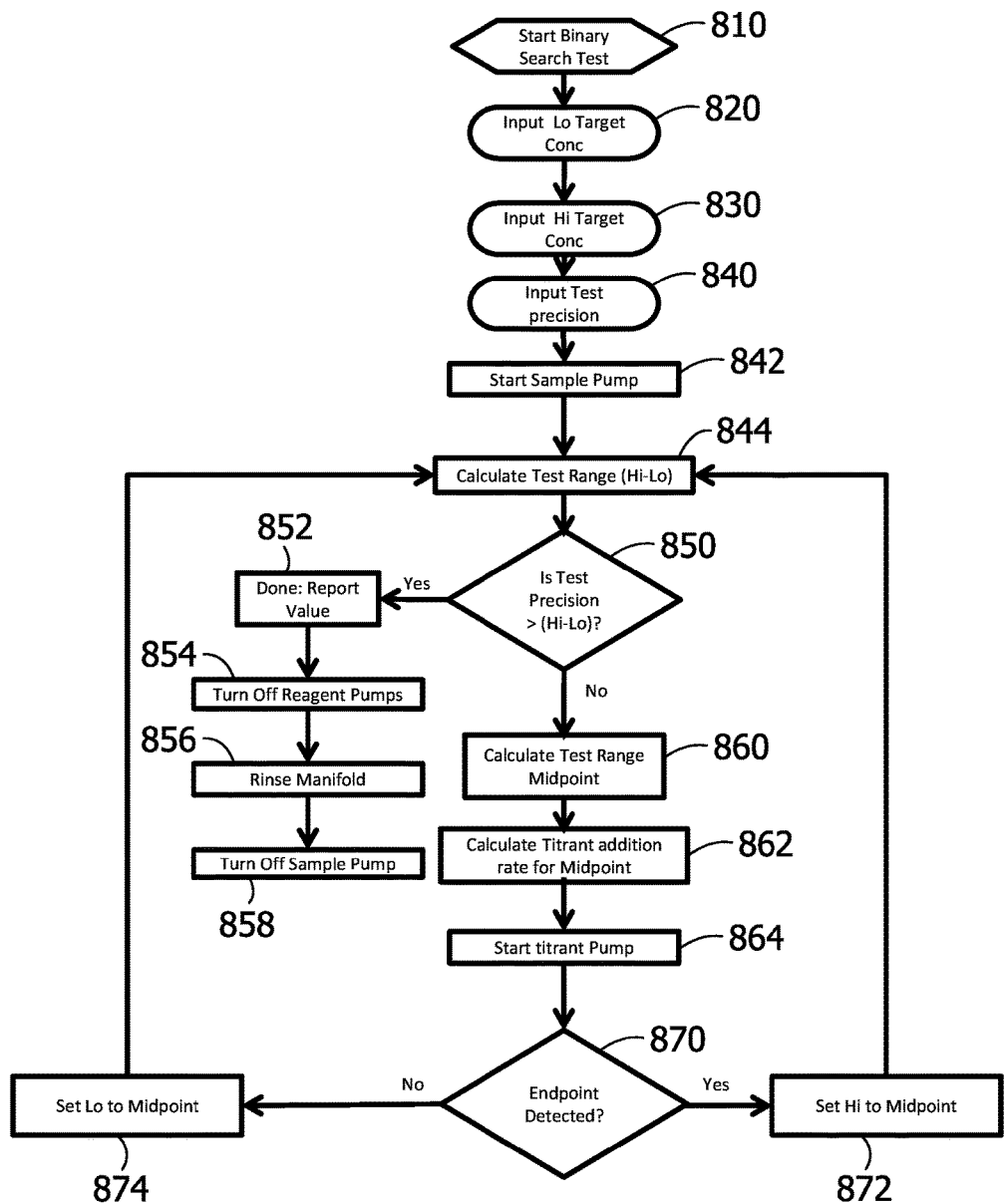
FIG. 3 is a process flow diagram for measuring whether a target analyte concentration is within a specified concentration range as compared to the test precision required.

FIG. 3 is a process flow diagram of a Binary Search Window method for quantification of a target analyte concentration in a process solution wherein the PLC is started 810, and a first low estimated target analyte concentration and a first high estimated target analyte concentration are determined and input into the PLC 820, 830. A test precision value is determined and input into the PLC 840. Then, the sample pump is started 842, and the first test range of the difference between the first high estimated target analyte and the first low estimated target analyte concentration is calculated 844. It is then determined whether the test precision value is greater than the first test range 850, and if the test precision value is greater than the first test range, then the value is reported 852. The sample and reagent pumps are then turned off 854, the manifold is rinsed 856, and the sample and regent pumps are turned off 858.

FIG. 3 further describes a process of determining whether the test precision value is greater than the first test range 850, and if the test precision value is not greater than the first test range, then calculating the first test range midpoint 860. Then, calculating a first midpoint flow rate of the titrant based on the first test range midpoint of the estimated target analyte concentration 862, and starting the titrant pump to introduce the titrant at the first midpoint flow rate 864. Then, determining whether the endpoint of the reaction between the target analyte and the titrant can be detected 870, and if the endpoint can be detected, setting a second high estimated target analyte concentration to the first test range midpoint 872. Then, calculating the second test range of the difference between the second high estimated target analyte and the first low estimated target analyte concentration 844, and determining whether the test precision value is greater than the second test range 850, and if the test precision value is greater than the second test range, then the value is reported 852, and the pumps are turned off and the manifold is rinsed as above.

FIG. 3 also describes a process of determining whether the endpoint of the reaction between the target analyte and the titrant can be detected 870, and if the endpoint cannot be detected, setting the second low estimated target analyte concentration to the first test range midpoint 874, and calculating the third test range of the difference between the second low estimated target analyte and the first low estimated target analyte concentration 844. Then, determining whether the test precision value is greater than the third test range 850, and if the test precision value is greater than the third test range, then reporting the value 852.

FIG. 3 further includes in the process where the steps of comparing the test range to the test precision 850, calculating the test range midpoint 860, detecting the endpoint 870, and recalculating the test range 872, 874, until the test precision value is greater than the new test range, then reporting the value 852 and turning off the reagent pumps 854, rinsing the manifold 856, and turning off the sample pump 858.

The method as described in FIG. 3 wherein the target analyte is peroxyacetic acid, peroxide, or a combination thereof.

The method as described in FIG. 3 wherein the titrant is thiosulfate.

The method as described in FIG. 3 wherein potassium iodide, acetic acid, starch indicator, or a combination thereof is added to the peroxyacetic acid and/or peroxide solution. The methods as described herein where potassium iodide, acetic acid, starch indicator, or a combination thereof are the conditioning reagent or reagents.

Figure 4:
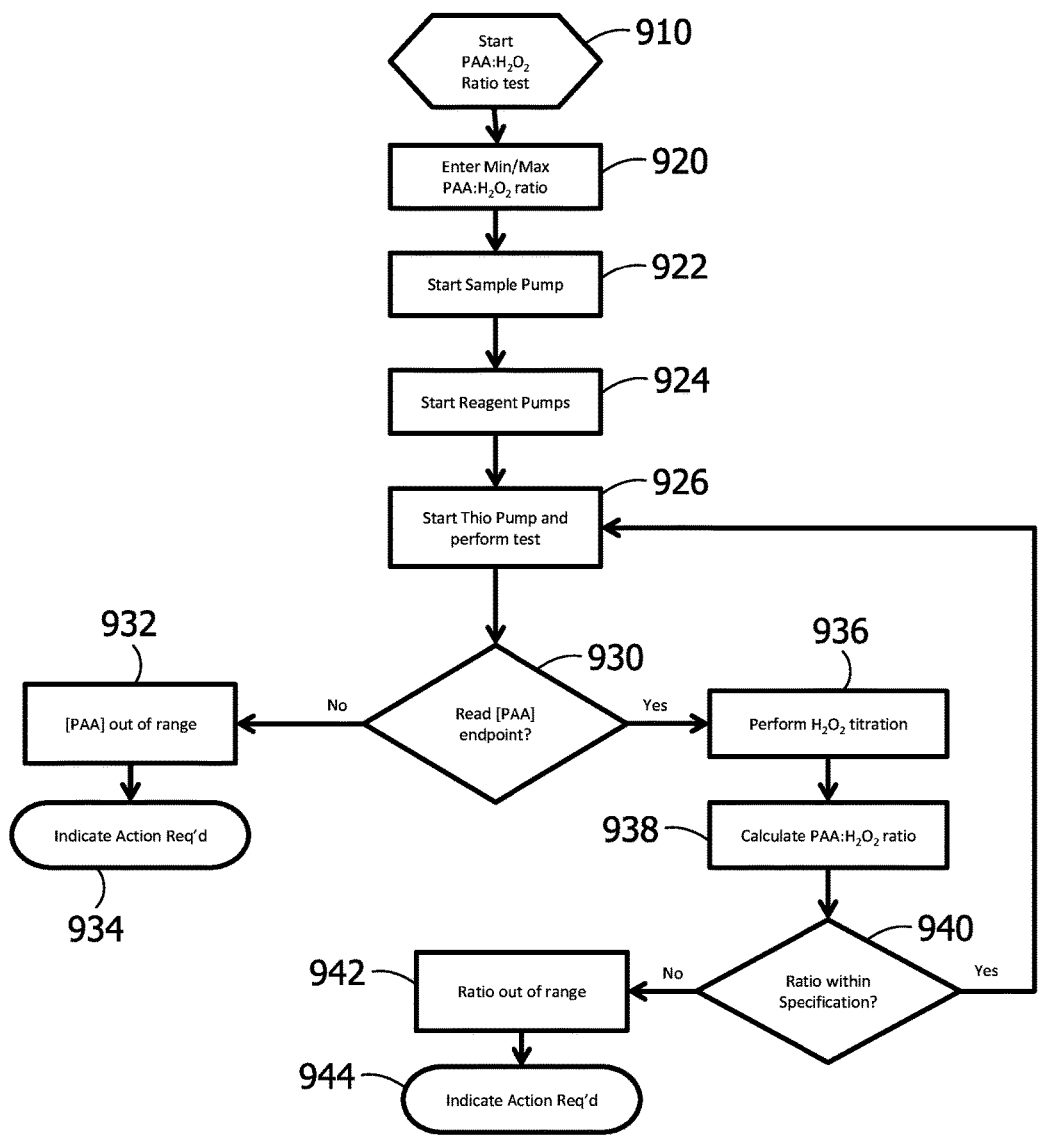
FIG. 4 is a process flow diagram for measuring the peroxyacetic acid (PAA) to peroxide ratio.

FIG. 4 is a process flow diagram of a process for determining the ratio of two agents in a sample, for example, for determining the ratio of peroxyacetic acid (PAA) to peroxide ($H_2O_2$). The PLC is started 910 and a minimum and maximum PAA:$H_2O_2$ ratio is input into the PLC 920. The sample and reagent pumps 922 & 924 are started and the titrant pump (containing thiosulfate) is started to start the test 926. It is then determined whether the PAA endpoint can be detected 930 and if the PAA endpoint can be detected, then the remaining H2O2 concentration in the sample is titrated with additional thiosulfate 936, and the PAA:$H_2O_2$ ratio is calculated 938 from the titration results of the PAA and $H_2O_2$ titrations. If the PAA:$H_2O_2$ ratio is within the minimum and maximum PAA:$H_2O_2$ ratios input into the PLC 940, then after a prescribed time interval the test is run over again to determine whether the PAA:$H_2O_2$ remains within the minimum and maximum PAA:$H_2O_2$ ratios as time progresses.

If the PAA:$H_2O_2$ ratio is not within the minimum and maximum PAA:$H_2O_2$ ratios input into the PLC 940, then the PAA:$H_2O_2$ ratio is out of range 942 and following the proper action 944 of, for example, aseptic bottle filling, draining the sample tank containing the PAA/$H_2O_2$, and preparing a fresh sample and repeating the process starting with starting the titrant pump and performing the test 926.

FIG. 4 further describes the process wherein when the PAA endpoint is not detected 930, and the PAA concentration is out of range of the detector 932 followed by a prompt indicating that action is required 934. The process then includes a proper action of for example, aseptic bottle filling, draining the sample tank containing the PAA/$H_2O_2$, and preparing a fresh sample and repeating the process starting with starting the titrant pump and performing the test 926.

Figure 5:
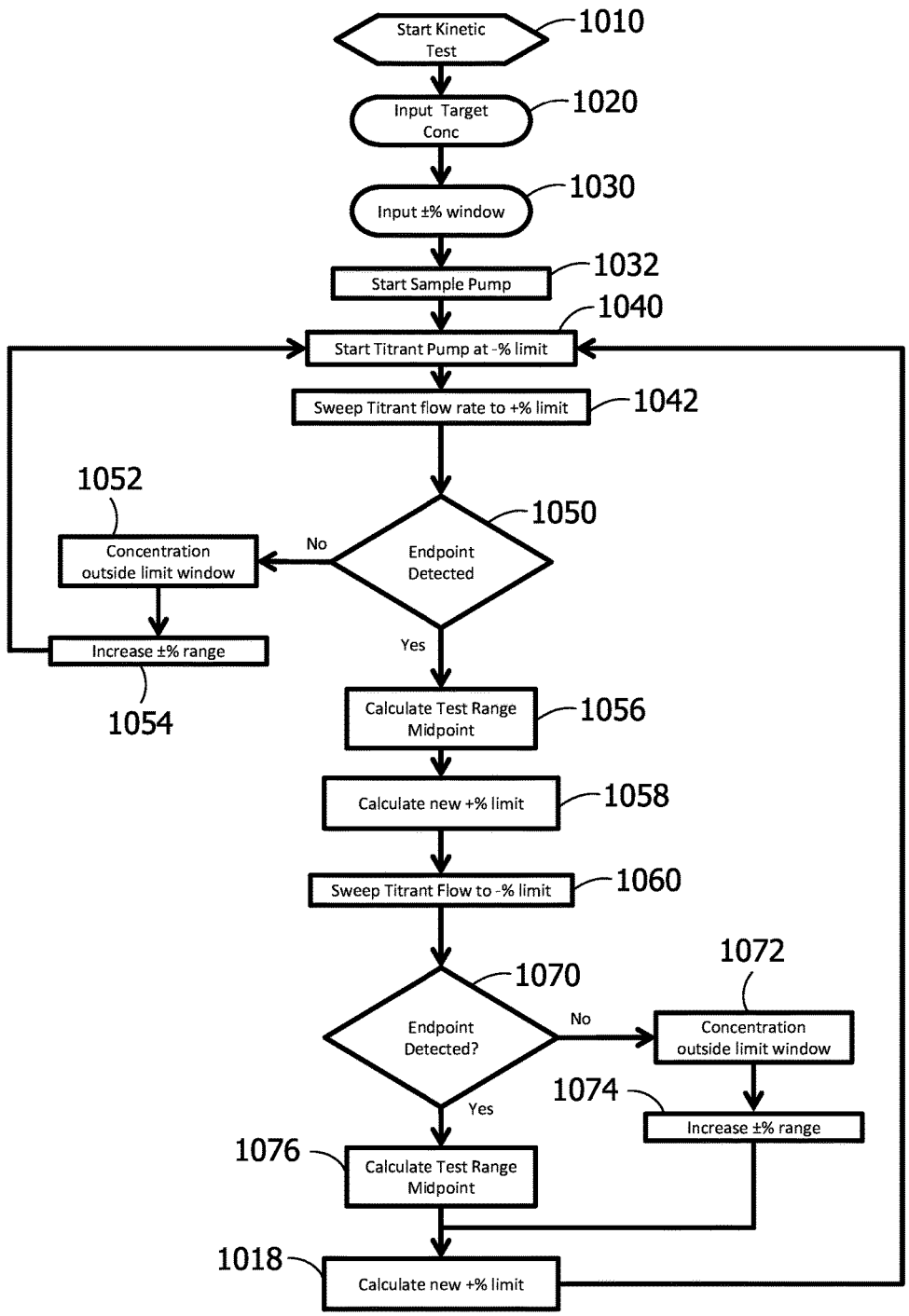
FIG. 5 is a process flow diagram for measuring the rate of a titration reaction.

FIG. 5 is a process flow diagram of a Kinetic method for quantification of a target analyte concentration in a process solution wherein the PLC is started 1010, determining an estimated target analyte concentration and inputting the value in the PLC 1020. Then, calculating a first target analyte concentration range that is the difference between a first low estimated target analyte concentration and a first high estimated target analyte concentration, wherein the first low estimated target analyte concentration is calculated by subtracting a certain percentage value from the estimated target analyte concentration and the first high estimated target analyte concentration calculated by adding the same certain percentage value to the estimated target analyte concentration and inputting this value into the PLC 1030. Starting the sample pump 1032, and calculating a first low titrant flow rate based on the first low estimated target analyte concentration and calculating a first high titrant flow rate based on the first high estimated target analyte concentration, and starting the titrant pump and introducing the titrant to the process solution at the first low titrant flow rate 1040 and gradually increasing the titrant flow rate to the first high titrant flow rate 1042. Then, determining whether the endpoint of the reaction between the target analyte and the titrant can be detected 1050, and if the endpoint cannot be detected, then the actual target analyte concentration is outside the first target analyte concentration range 1052, and increasing the first target analyte concentration range 1054 and repeating sweeping the flow rate from its lower 1040 to upper 1042 limit and increasing the test range 1054 until the endpoint can be detected.

FIG. 5 further describes a process of determining whether the endpoint of the reaction between the target analyte and the titrant can be detected 1050, and if the endpoint can be detected, calculating the first target analyte concentration midpoint 1056 and setting a second high estimated target analyte concentration to the first target analyte concentration midpoint 1058. Then, calculating a second high flow rate based on the second high estimated target analyte concentration, and introducing the titrant to the process solution at the second high titrant flow rate and gradually decreasing the titrant flow rate to the first low titrant flow rate 1060. Then, determining whether the endpoint of the reaction between the target analyte and the titrant can be detected 1070, and if the endpoint cannot be detected, the analyte concentration is outside the concentration range 1072, and increasing the first target analyte concentration range 1074 and repeating sweeping the flow rate from its lower 1040 to upper 1042 limit and increasing the test range 1054 until the data collected is sufficient for the intended purpose. If the endpoint 1070 can be detected, then the test range midpoint is calculated 1076 and a second target analyte concentration midpoint is calculated 1018.

For the methods described in FIGS. 1-5, the target analyte can comprise hydrogen peroxide, a peroxyacetic acid, performic acid or a combination thereof. Preferably, the target analyte comprises hydrogen peroxide, peroxyacetic acid, or a combination thereof.

For the methods described in FIGS. 1-5, the titrant comprises thiosulfate.

For the methods described herein, the conditioning reagent comprises potassium iodide, acetic acid, starch indicator, or a combination thereof.

In each method described herein, the actual target analyte concentration can be directly detected or the actual target analyte concentration can be calculated from the detection of the concentration of a product of the reaction of the target analyte and the titrant.

The process is such that it can be implemented anywhere, such as at a sampling point in a processing facility or other industrial or commercial location not conducive to regularly performing standard titrations.

Additionally, the entire process can be completed in a short time; approximately 2 minutes and 40 seconds. Prior to rinsing and preparing the system to take another measurement, amount can be determined in less time; approximately 1 minute and 20 seconds.

The methods described herein can further include a calibration step. Calibration steps can be performed in-line, calibrating flow rates, measurements, and the like. Calibrations can be performed prior to every titration to provide increased accuracy to the measurement. A calibration can be performed after a predetermined number of measurements, or can be prompted by a user. In-line calibrations can be performed without substantially slowing down the analysis procedure. Such calibration can include injection of a sample of known concentration and confirming that the system measures the concentration accurately. To the extent the measurement is inaccurate, the system could self-adjust in order to accurately measure the sample of known concentration.

When the methods described herein are directed toward determining the concentration of oxidizers present in the sample and the sample is chilled, the reaction of the peroxide will be suppressed, therefore allowing for the determination of the peracid concentration in the sample. Thus, a chilled sample can be used in the continuous process to suppress peroxide reactions and calculate a peracid concentration. In some configurations, the sample is already chilled for purposes other than titration, and the peroxide reaction can be suppressed without need for further chilling. Other chilling means can be employed into the system to intentionally cool the sample.

Once a chilled sample has been titrated to determine a peracid concentration, a catalyst (such as the aforementioned ammonium molybdate) and strong acid (such as sulfuric acid) can be substituted for the weak acid in the combination of reagent. As previously described, the mixing of such components into the sample will cause the peroxide reaction to no longer be suppressed, allowing for both peracid and peroxide reactions. It is noteworthy that in the continuous mode, as time progresses, fresh sample is continuously brought into the system. As a result, despite possibly already determining a peracid concentration using a chilled sample, subsequent titrations including the catalyst and strong acid will involve reactions from both the peroxide and the peracid, since in the fresh sample, the peracid has not undergone a reaction. This is contrary to the batch mode, wherein after determining the peracid content, only the peroxide was left to react.

Thus, when titrating a solution of sample and reagents including a catalyst and strong acid, the amount of oxidizer that will be calculated will comprise both peracid and peroxide together. Accordingly, the difference between the total oxidizer concentration and the peracid concentration (calculated previously by suppressing the peroxide reaction) will yield the peroxide concentration of the sample. Both reactions (with weak acid and with a strong acid and catalyst) can be performed in succession, and in any permutation, since fresh sample is continuously used by the system. The reactions can be done in parallel, wherein the sample is split into two lines and titrated. One in which peroxide reaction is suppressed and one in which it is not. Simultaneous measurement of peracid and total oxidizer concentrations can then be performed, and a subtraction step will additionally yield the peroxide concentration. It should be noted that, while cooling the sample can advantageously suppress the peroxide reaction, temperature changes can have alternative effects on alternative chemistries and titrations, as well as on viscosities and flow rates of components used in, for example, a continuous flow process.

Alternatively, the optical sensor can signal transparency once it senses any radiation from the light source. Such systems can be used if the color change is sufficiently stark, such as the blue-black to transparent as described above, for example. It should be noted, however, that with proper optical equipment, such a stark color change may not be necessary in order for the optical arrangement to be able to accurately detect a titration endpoint. Not all reagents may be necessary. For example, the starch indicator can be omitted with the inclusion of certain optics in the optical arrangement.

A further aspect of the invention is a dynamic window monitoring method for quantification of a target analyte concentration in a process solution comprising (a) inputting a low estimated target analyte concentration, a high estimated target analyte concentration, and a maximum integer value for a data counter, (b) setting the data counter to 1, (c) calculating a first target analyte concentration by dividing the sum of the low estimated target analyte concentration and the high estimated target analyte concentration by 2, (d) calculating a first target analyte flow rate based on the first target analyte concentration and introducing a titrant at the first target analyte flow rate, (e) measuring a first target analyte signal value that correlates to the actual target analyte concentration, (f) comparing the first target analyte signal value to a threshold target analyte signal value and a maximum target analyte signal value, and if the first target analyte signal value is between the threshold target analyte signal value and the maximum target analyte signal value, entering the first target analyte concentration and the first target analyte signal value as a first data pair into a data array, (g) if the data pair is entered into the data array, then increasing the data counter by 1, or if the data pair is not entered into the data array, repeating steps (c) to (f) with the data counter at the same value, (h) calculating a next target analyte concentration using the equation:

$$C_{l+1} = C_l + \frac{C_{max} - C_{min}}{n} \quad (1)$$

where n is the maximum integer value for the data counter, $C_{l+1}$ is the next target analyte concentration, $C_l$ is the previous target analyte concentration, $C_{max}$ is the high estimated target analyte concentration or the concentration calculated from equation 3 and $C_{min}$ is the low estimated target analyte concentration or the concentration calculated from equation 4, wherein if the next target analyte concentration, $C_{l+1}$ is greater than $C_{max}$, then $C_{l+1}$ is set to equal $C_{min}$, (i) calculating a next target analyte flow rate based on the next target analyte concentration and introducing a titrant at the next target analyte flow rate, (j) measuring a next target analyte signal value that correlates to the actual target analyte concentration, (k) comparing the next target analyte signal value to a threshold target analyte signal value and a maximum target analyte signal value, and if the next target analyte signal value is between the threshold target analyte signal value and the maximum target analyte signal value, entering the next target analyte concentration and the next target analyte signal value as a next data pair into the data array, (l) if the next data pair is entered into the data array, then increasing the data counter by 1, or if the next data pair is not entered into the data array, repeating steps (i) to (k) with the data counter set to the same value, (m) repeating steps (h)-(l) until the number of data pairs entered into the data array equals the maximum value for the data counter, (n) calculating $\Sigma x$, $\Sigma x^2$, $\Sigma y$, $\Sigma y^2$, and $\Sigma xy$ wherein x is the target analyte concentration and y is the signal value for each data pair, (o) calculating SXX, SYY, and SXY using the following equations:

$$SXX = \Sigma x^2 - \frac{(\Sigma x)^2}{n}, \quad (2a)$$

$$SYY = \Sigma y^2 - \frac{(\Sigma y)^2}{n}, \text{ and} \quad (2b)$$

$$SXY = \Sigma xy + \frac{(\Sigma x)(\Sigma y)}{n}, \quad (2c)$$

(p) calculating an endpoint concentration at (i) a minimum target analyte signal value when the target analyte concentration is inversely proportional to the target analyte signal value or (ii) a maximum target analyte signal value when the target analyte concentration is directly proportional to the target analyte signal value using the following equation:

$$C_{max} = \frac{\Sigma x}{n} - \left(\frac{SXX}{SXY}\right) \cdot \left(\frac{\Sigma y}{n}\right), \quad (3)$$

(q) calculating a minimum concentration at (i) a maximum target analyte signal value when the target analyte concentration is inversely proportional to the target analyte signal value or (ii) a minimum target analyte signal value when the target analyte concentration is directly proportional to the target analyte signal value using the following equation:

$$C_{min} = \left(\frac{SXX}{SXY}\right) \cdot \left(A_m - \frac{\Sigma y}{n} + \left(\frac{SXY}{SXX}\right) \cdot \frac{\Sigma x}{n}\right), \quad (4)$$

wherein $A_m$ is the target analyte signal value, (r) repeating steps (h)-(l) and reassigning the data pair designations so the first data pair entered is the first data pair replaced, (s) repeating steps (n)-(r) until the reaction endpoint is reached or the process is stopped.

The target analyte signal value for the dynamic window monitoring method can be an absorbance value, a fluorescence value, a conductance value, a redox potential value, a turbitity value, or an electrochemical value. Preferably, the analyte signal value is an absorbance value.

When the target analyte signal value for the dynamic window monitoring method is an absorbance value, the threshold value of absorbance of the process solution can be from about 0.01 to about 0.1.

The maximum integer value for the data counter for the dynamic window monitoring method can be 3, 4, 5, 6, 7, 8, 9, or 10. Preferably, the maximum integer value for the data counter can be 3, 4, or 5; most preferably, the maximum integer value for the data counter can be 3.

When the maximum integer value for the data counter is 3 for the dynamic window monitoring method, equation 1 can be:

$$C_{l+1} = C_l + \frac{C_{max} - C_{min}}{3}.$$

When the maximum integer value for the data counter is 3 for the dynamic window monitoring method, equation 2a, 2b, and 2c can be:

$$SXX = \Sigma x^2 - \frac{(\Sigma x)^2}{3} \quad (2a)$$

$$SYY = \Sigma y^2 - \frac{(\Sigma y)^2}{3}, \text{ and} \quad (2b)$$

$$SXY = \Sigma xy + \frac{(\Sigma x)(\Sigma y)}{3}. \quad (2c)$$

When the maximum integer value for the data counter is 3 for the dynamic window monitoring method, equation 3 can be:

$$C_{max} = \frac{\Sigma x}{3} - \left(\frac{SXX}{SXY}\right) \cdot \left(\frac{\Sigma y}{3}\right).$$

When the maximum integer value for the data counter is 3 for the dynamic window monitoring method, equation 4 can be:

$$C_{min} = \left(\frac{SXX}{SXY}\right) \cdot \left(A_m - \frac{\Sigma y}{3} + \left(\frac{SXY}{SXX}\right) \cdot \frac{\Sigma x}{3}\right).$$

The target analyte concentration for the dynamic window monitoring method can be inversely proportional to the target analyte signal value.

The target analyte concentration for the dynamic window monitoring method can be directly proportional to the target analyte signal value.

Particularly, the type of titration and signal value can vary since the slope, intercept, and extrapolated concentrations are based on the signal values. Thus, the least squares regression analysis employed facilitates the estimation of $C_{max}$ and $C_{min}$ regardless of the slope of the transition in the signal value.

Specifically, the dynamic window monitoring method allows for titrations from light to dark or dark to light when using an absorbance signal since the least squares regression analysis employed facilitates the estimation of $C_{max}$ and $C_{min}$ regardless of the slope of the transition in the absorbance values.

The target analyte for the dynamic window monitoring method can comprise hydrogen peroxide, a peroxyacetic acid, performic acid or a combination thereof.

The titrant for the dynamic window monitoring method can comprise thiosulfate.

Specifically, when the signal value is an absorbance value, when the maximum integer value for the data counter is 3, and when the absorbance value at the endpoint of the titration is less than the absorbance value at the starting point of the titration, the following general process can be used.

1. Read user-defined minimum and maximum window concentrations;
2. Read threshold absorbance ($A_{thresh}$) value and maximum absorbance ($A_{max}$);
3. Set data counter (cnt) to 1;
4. Calculate midpoint concentration (C) to test using the following equation:

$$C = \frac{C_{max} + C_{min}}{2};$$

5. Sample Loop:
    a. Measure absorbance A at concentration C;
    b. If absorbance (A) measured is greater than the threshold absorbance ($A_{threshold}$) then
        i. load A and C to data array;
        ii. increment counter, cnt (limited to 3 data points);
    c. If counter (cnt) greater than or equal to 3 then when $A_{thresh} < A_1 < A_{max}$, where $A_{thresh} = 0.02$ and $A_{max} = 0.25$):
        i. Calculate:
        $\Sigma x, \Sigma x2, \Sigma y, \Sigma y2, \Sigma xy$ for valid data points
        ii. Calculate:

$$1.\ SXX = \Sigma x^2 - \frac{(\Sigma x)^2}{3}$$

$$2.\ SYY = \Sigma y^2 - \frac{(\Sigma y)^2}{3}$$

$$3.\ SXY = \Sigma xy + \frac{(\Sigma x)(\Sigma y)}{3}$$

iii. Calculate endpoint sample concentration at A=0 ($C_{A=0}$) using equation A (for Excel calculations) or equation 3 below:

$$C_{max} = C_{A=0} = \frac{\text{intercept}(A_{cnt-2},\ A_{cnt-1},\ A_{cnt},\ C_{cnt-2},\ C_{cnt-1},\ C_{cnt})}{\text{slope}(A_{cnt-2},\ A_{cnt-1},\ A_{cnt},\ C_{cnt-2},\ C_{cnt-1},\ C_{cnt})} \quad (A)$$

$$C_{max} = C_{A=0} = \frac{\Sigma x}{3} - \left(\frac{SXX}{SXY}\right) \cdot \left(\frac{\Sigma y}{3}\right); \quad (3)$$

iv. Calculate minimum concentration ($C_{min}$) at $A_{max}$ using equation B (for Excel calculation) or equation 4 below:

$$C_{min} = C_{A_{max}} = \frac{(A_{max} - \text{intercept}(\{A_1, A_2, A_3\}, \{C_1, C_2, C_3\}))}{\text{slope}(\{A_1, A_2, A_3\}, \{C_1, C_2, C_3\})} \quad (B)$$

$$C_{min} = C_{A_{max}} = \left(\frac{SXX}{SXY}\right) \cdot \left(A_{max} - \frac{\Sigma y}{3}\right) + \left(\frac{SXY}{SXX}\right) \cdot \frac{\Sigma x}{3}; \quad (4)$$

v. Move data in sliding window:
            1. A1=A2; A2=A3
            2. C1=C2; C2=C3
        vi. Set counter (cnt) to 3
    d. Calculate new test concentration $C_{1+1}$:

$$C_{I+1} = C_I + \frac{C_{max} - C_{min}}{3};$$

e. If $C_{1+1}$ is greater than $C_{max}$ then $C_{1+1} = C_{min}$;
    f. Back to 5.a. and repeat sample loop until titration complete or method stopped.

The dynamic window monitoring method is detailed in example 2.

Titration Systems

Figure 6:
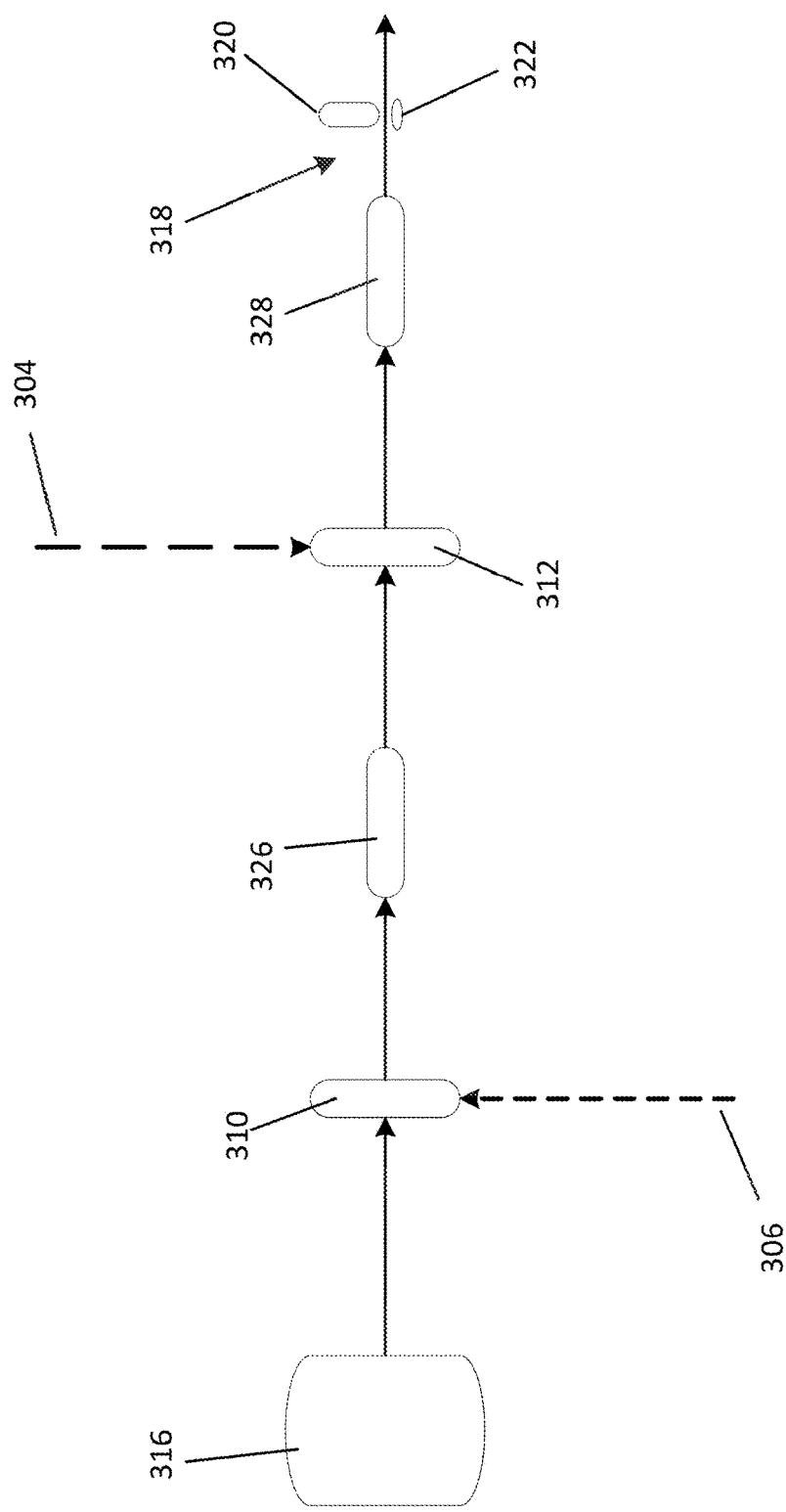
FIG. 6 is a schematic diagram of a continuous-mode automatic titrator.

FIG. 6 is a schematic diagram of a continuous-mode automatic titrator. Here, the sample 316 flows through a line, which can referred to as a reaction vessel, at some known rate into a first manifold 310, where it encounters reagents 306 that combine with the sample 316. A wide variety of reagents known for standard titrations can be used, and a sufficient addition of reagents 306 will cause the sample 316 to change. In this continuous-mode operation, however, the determining factor of "sufficient addition of reagents" corresponds to the rate of reagent addition. This is because the sample 316 is flowing through the system continuously so fresh sample 316 is continuously fed into the first manifold 310. Accordingly, if the reagents 306 are added too slowly, they will fail to adequately react with the entire sample 316 and the sample 316 may not change. Put another way, in a given amount of time, a certain volume of sample 316 will flow through a particular point in the system. In order to achieve the desired change, then, there needs to be an appropriate volume of reagent 306 that also flows past this point during the same time, which corresponds to a sufficient flow rate. The sample 316 and reagents 306 can be mixed in a mixer 326.

Thus, an excess flow rate or reagent 306 is used in order to assure that the amount of sample flowing is the limiting factor in the reaction to cause the change. This is analogous to utilizing an excess volume of reagent in batch-mode as has been previously discussed. Once the sample 316 and reagents 306 have combined in the first manifold 310 to form a solution, this solution continues to flow through the system. A wide variety of detectors can be used including detectors that detect a spectrophotometric change, an electrochemical change, or a pH change.

Some systems comprise an optical arrangement 318, such as a light source 320 and an optical sensor 322, which senses radiation emitted from the light source 320 after it travels through the solution path. Accordingly, the optical arrangement 318 can determine whether or not the solution has sufficiently changed color before attempting a titration. This can be sensed by a user in a manual operation or can be controlled by a PLC in an automated system. If the solution is sensed as having not achieved the desired change, e.g., turned to the desired color, the flow rate of the reagents can be increased or the flow rate of the sample decreased in order to increase the reagent-to-sample ratio. Alternatively, the lack of a change, e.g., color change, can trigger an alarm to cease operation of the system, possibly indicating that the reservoir of one or more reagents can have run out or that the sample lacks the target analyte expected to be therein.

Once the sample 316 and reagents 306 have mixed, and the resulting solution has been determined to have undergone a change, e.g., color change, titrant 304 can be added, using a second manifold 312, for example. Titrant 304 can be mixed in to the solution by a mixer 328. Similarly to the incorporation of reagents 306, the flow rate of the titrant 304 is analogous to the amount of titrant added to the sample in a batch mode. Again, a wide variety of standard titrants can be used. Therefore, at an appropriate flow rate of titrant 304 into the flowing solution, the titration should reach an endpoint of the reaction of the target analyte with the titrant.

To reach a meaningful endpoint yielding accurate results, the lowest flow rate resulting in viewing the change, e.g., color change, should be used. This is because if the flow rate of the titrant 304 is too high (i.e. above the minimum to achieve the change, e.g., color change, or other detectable endpoint), the characteristic of the endpoint can still be observed. For example, the addition of too much sodium thiosulfate in the batch mode would still result in a transparent sample even though an excess of titrant was used, since the same endpoint could have been achieved at a lesser dose.

The process can be automated by a controller such as a programmable logic controller (PLC), using feedback mechanisms from the detector.

The flow rate of the titrant can be changed by an amount that is nonlinear over time. An exponential increase in flow rate, for example, will begin by making small changes in the flow rate while the concentrations involved are small. Over time, as the concentrations become larger (since the flow rate has continued to increase), small changes in flow rate become unnecessarily precise compared to the concentrations at hand and the flow rate can increase by larger amounts.

A low concentration of peroxide and peracid can be accurately resolved by the small changes in concentrations early in the process, while large concentrations of peracid and/or peroxide can be titrated in a shorter amount of time since the rate of titrant addition increases more rapidly over time.

Figure 7:
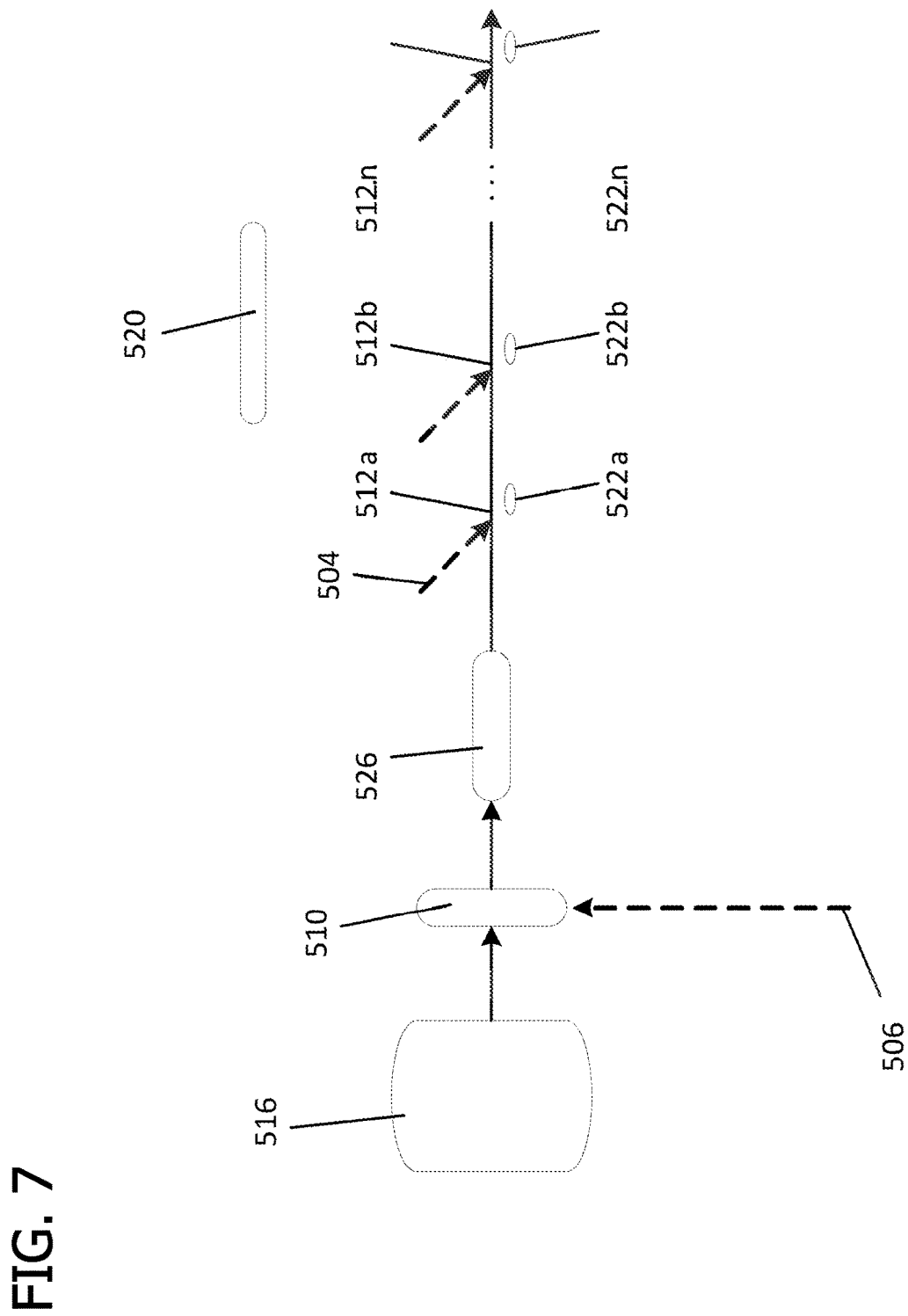
FIG. 7 is a schematic diagram of an alternative embodiment of the invention comprising multiple titrant injection points.

Alternatively, multiple injection points of the titrant can be included in the system in order to determine the endpoint of the reaction. FIG. 7 is a schematic diagram of an alternative system comprising multiple titrant injection points. Sample 516 flows and mixes with reagents 506 in a first manifold 510, and possibly in a mixer 526. The titrant 504 is added at multiple titrant injection points 512*a* . . . 512*n* in the flow path of the solution, with detectors such as optical sensors 522*a* . . . 522*n* arranged nearby and downstream from each injection point 512. After each subsequent addition, the amount of titrant in the solution increases, and the solution is monitored by the detector, such as an optical sensor 522. Accordingly, after a certain number of injection points, a sufficient amount of titrant to reach the endpoint can be reached and will be sensed by the optical sensor 522 disposed after the injection point 512 causing the endpoint to be reached. The combined flow rate of titrant at the endpoint can be determined and the desired sample concentration calculated.

In another alternative system, multiple titrant injection points can be disposed along a line in which a solution comprising the sample and reagent is flowing. Each injection point 512 can have associated with it an optical sensor 522 for measuring a parameter such as color or intensity of light emitted from a light source 520 on the other side of the line through which the sample is flowing. Each optical sensor 522 is located downstream from its associated injection point 512. Such an arrangement is possible with a single or with multiple light sources 520 providing light to the sensors.

For this alternative system, as sample flows through the line, titrant is added at each injection point 512, the flow rate of the titrant differing between points. Thus, a sufficiently high titrant flow rate will result in the sample being completely titrated and changing color. If, at any particular injection point 512, titrant is injected at a sufficiently high flow rate, the solution immediately at or after the injection point 512 will undergo the color change associated with that titration.

The system can be configured so that the optical system comprising the light source 520 and plurality of optical sensors 522*a* . . . 522*n* can detect the color change associated with the titration. Thus, if the color change happens at a particular injection point 512, the optical sensor 522 associated with that point can sense the occurrence of the endpoint of the titration and indicate that the titrant flow rate at that particular injection point 512 is at least sufficient to titrate the sample. If an array of injection points 512*a* . . . 512*n* is used with each point having a different titrant flow rate, it can be determined that the flow rate corresponding to the endpoint of titration lies between the highest flow rate not resulting in titration and the lowest flow rate that does result in titration. Smaller differences in flow rates between injection points 512*a* . . . 512*n* will lead to a more accurate determination of the flow rate corresponding to the titration endpoint. Once this flow rate is determined, the methodology described above can be used to calculate the concentration of the desired component of the sample.

An advantage of this method is that, with a fast enough optical arrangement, the analysis at each injection point can be done very quickly. Thus, only a small amount of titrant needs to be added at each point to determine whether or not the flow rate is sufficient for complete titration, and an overall small amount of titrant is needed to determine an endpoint. This process can be automated by a device such as a PLC in similar ways as described relating to alternatives, wherein the controller can control the flow rates of the sample and titrants, detect the titration by means of the optical arrangement, and calculate the concentration from the flow rates. In this embodiment, the controller performs the additional task of determining a "cut-off" point, above which titration occurred and below which it did not.

Having described the invention in detail, it will be apparent that modifications and variations are possible without departing from the scope of the invention defined in the appended claims.

EXAMPLES

The following non-limiting examples are provided to further illustrate the present invention.

Example 1

Binary Search Window Method

Figure 8:
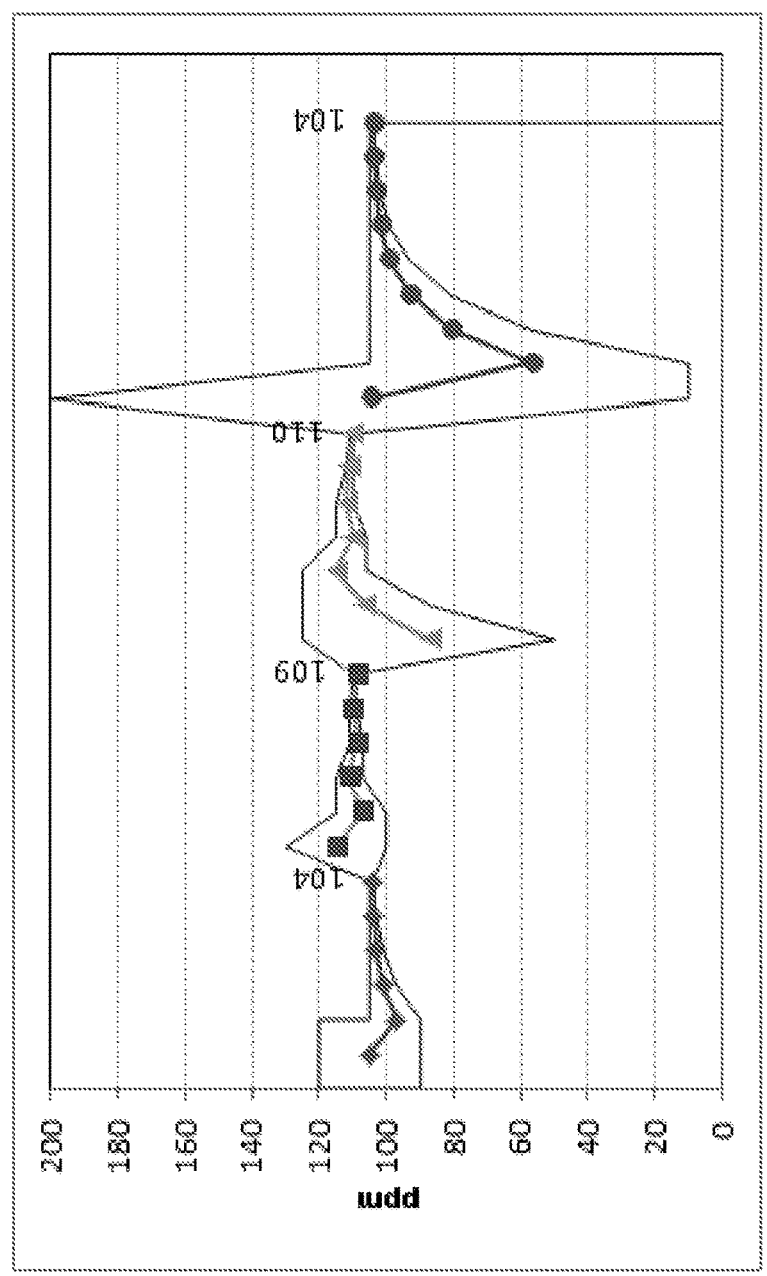
FIG. 8 is a graph of the titration course versus the concentration of target analyte for a sample having a concentration of 104 ppm of the target analyte.

FIG. 8 is an example plot of actual titration results. In this example the sample and reagent pumps ran continuously at fixed rates. The titrant was 0.1 N thiosulfate and the pumping rate was varied within the windows/ranges depicted in the mathematical model disclosed below. The pumping rate was calculated to deliver the minimum to maximum amount of titrant in ppm as listed in the table. The sample for the test was diluted with water to provide 104 ppm of peroxyacetic acid. The sample containing peroxyacetic acid and peroxide solution was commercially available as TSUNAMI® 100 (30-60% acetic acid, 15.2% peroxyacetic acid, 11.2% hydrogen peroxide) from Ecolab, Inc., St. Paul, Minnesota. Potassium iodide, acetic acid, and starch indicator were also added to the sample flow to aid detection of the endpoint of the reaction of peroxyacetic acid with thiosulfate.

The area with border of FIG. 8 shows the window being tested for four titrations performed sequentially. As shown, the window narrowed with each step. The precision of the test was set to 1 ppm, meaning that the difference between the high and low range converged when the difference was less than or equal to 1 ppm. In this example, the result did not converge on the result because there was difficulty controlling the sample pump with the equipment used for the test. This method shows a binary search method. The mathematical model used for test is below.

| | Real numbers (ppm) | | | | |
|---|---|---|---|---|---|
| Iteration | Min | Max | Range | Test | N > Test? |
| 1 | 80.00 | 120.00 | 40.00 | 100.00 | TRUE |
| 2 | 100.00 | 120.00 | 20.00 | 110.00 | FALSE |
| 3 | 100.00 | 110.00 | 10.00 | 105.00 | FALSE |
| 4 | 100.00 | 105.00 | 5.00 | 102.50 | TRUE |
| 5 | 102.50 | 105.00 | 2.50 | 103.75 | TRUE |
| 6 | 103.75 | 105.00 | 1.25 | 104.38 | FALSE |

In this example the sample test concentration was 104 ppm and the initial window was set to a low of 80 ppm and a high of 120 ppm. In five iterations, the algorithm converged on the concentration of 103.75 ppm, well within prescribed 1 ppm resolution. In this example, "Min" is the minimum window, "Max" is the maximum window tested, and Range is the difference between the Min and Max. The value labelled Test is the concentration being evaluated, and N>Test represents the detector output indicating if the endpoint was reached.

Example 2

Dynamic Window Monitoring Method

Figure 9:
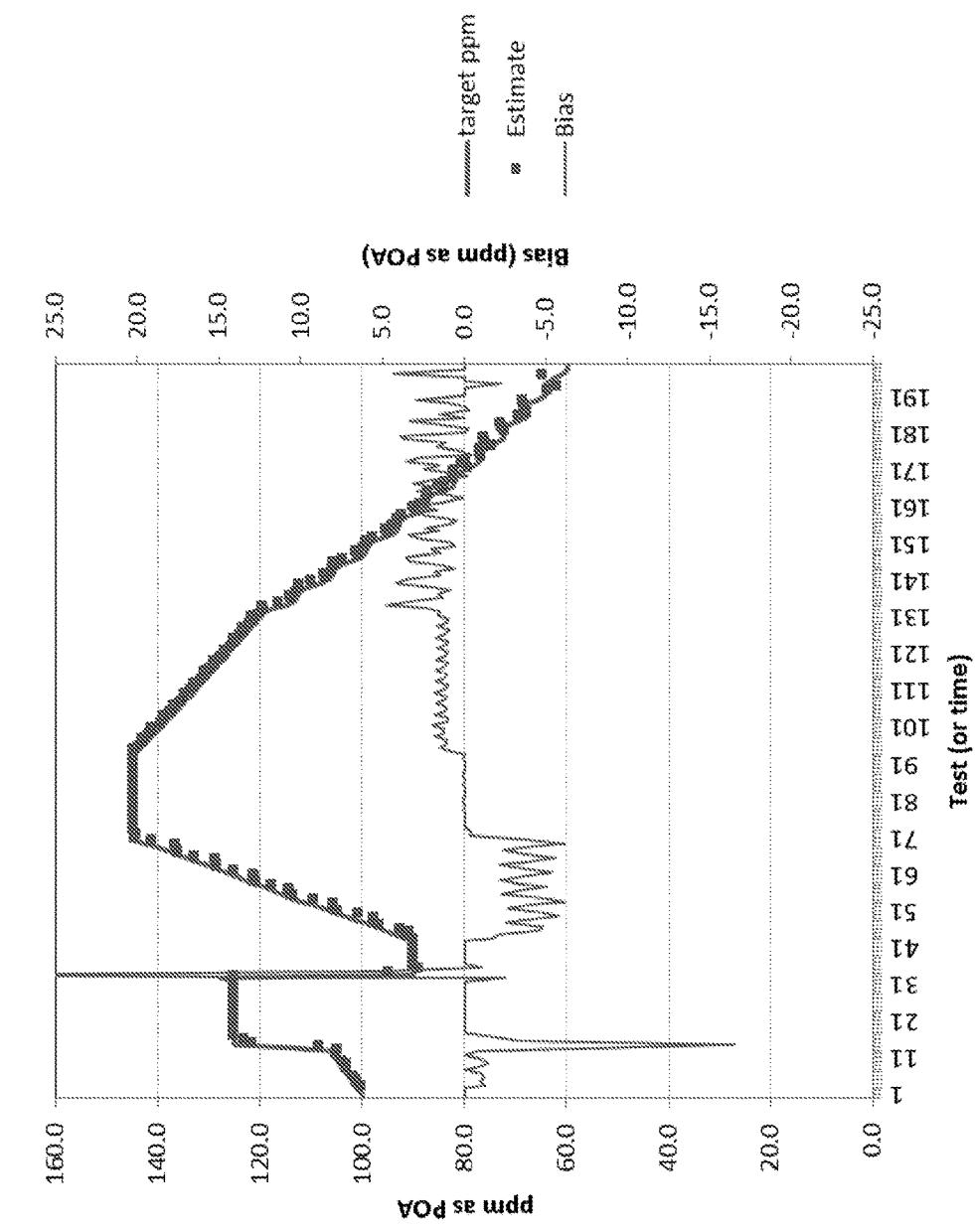
FIG. 9 is a graph of the titration in ppm versus time for the simulated data using a least squares regression analysis and shows that the concentration estimate follows the sample concentration. The bias of the method is also plotted versus time on the graph.

The sample concentration for the simulation represented in FIG. 9 started at 100 ppm, and varied from 60 to 145 ppm. The estimate, provided using the algorithm described herein in connection with the dynamic window monitoring method shows how the response follows the sample concentration in spite of wide variations in sample concentration. Random noise can be added to the test absorbance measurement to provide an additional stress to the algorithm. The bias, the difference between the estimate and sample ppm, can be calculated and has an average of 4 ppm. The simulated data for the first 50 points are shown below. Absorbance values in bold represent values less than the threshold absorbance and were not used in the regression analysis and the remaining absorbance values were greater than the threshold absorbance value and were used in the regression analysis.

| Sample ppm | ppm max | ppm min | Test ppm | Abs | Estimate | RSQ | Bias |
|---|---|---|---|---|---|---|---|
| 100.0 | 200.0 | 10.0 | 105.0 | 0.000 | | | |
| 100.5 | 200.0 | 10.0 | 168.3 | 0.000 | | | |
| 101.0 | 200.0 | 10.0 | 10.0 | 0.498 | | | |
| 101.5 | 200.0 | 10.0 | 73.3 | 0.154 | | | |
| 102.0 | 200.0 | 10.0 | 136.7 | 0.000 | | | |
| 102.5 | 200.0 | 55.2 | 10.0 | 0.480 | 102.4 | 0.9990 | −0.1 |
| 103.0 | 102.4 | 54.2 | 73.3 | 0.147 | 102.2 | 0.9998 | −0.8 |
| 103.5 | 102.2 | 53.9 | 10.0 | 0.485 | 101.1 | 0.9999 | −2.4 |
| 104.0 | 101.1 | 53.7 | 40.7 | 0.316 | 100.5 | 0.9998 | −3.5 |
| 104.5 | 100.5 | 55.0 | 71.1 | 0.171 | 103.7 | 0.9991 | −0.8 |
| 105.0 | 103.7 | 54.5 | 101.3 | 0.021 | 105.9 | 0.9999 | 0.9 |
| 105.5 | 105.9 | 54.5 | 10.0 | 0.466 | 105.9 | 1.0000 | 0.4 |
| 106.0 | 105.9 | 54.8 | 42.0 | 0.317 | 106.0 | 0.9999 | 0.0 |
| 112.5 | 106.0 | 55.5 | 73.9 | 0.161 | 107.8 | 0.9999 | −4.7 |
| 125.0 | 107.8 | 56.0 | 105.9 | 0.033 | 112.3 | 0.9983 | −12.7 |
| 125.0 | 112.3 | 50.1 | 10.0 | 0.403 | 115.0 | 0.9999 | −10.0 |
| 125.0 | 115.0 | 50.7 | 44.1 | 0.282 | 115.1 | 0.9995 | −9.9 |
| 125.0 | 115.1 | 53.2 | 79.1 | 0.158 | 123.6 | 1.0000 | −1.4 |
| 125.0 | 123.6 | 53.1 | 114.1 | 0.044 | 126.4 | 0.9997 | 1.4 |
| 125.0 | 126.4 | 55.1 | 10.0 | 0.413 | 125.1 | 0.9996 | 0.1 |
| 125.0 | 125.1 | 56.0 | 48.8 | 0.276 | 126.4 | 1.0000 | 1.4 |
| 125.0 | 126.4 | 54.8 | 87.2 | 0.129 | 122.8 | 0.9998 | −2.2 |
| 125.0 | 122.8 | 54.8 | 10.0 | 0.413 | 122.8 | 0.9998 | −2.2 |
| 125.0 | 122.8 | 54.8 | 47.6 | 0.280 | 122.8 | 0.9998 | −2.2 |
| 125.0 | 122.8 | 56.0 | 85.2 | 0.146 | 126.4 | 1.0000 | 1.4 |
| 125.0 | 126.4 | 10.0 | 122.8 | 0.003 | | | |
| 125.0 | 126.4 | 55.3 | 10.0 | 0.403 | 128.5 | 0.9997 | 3.5 |
| 125.0 | 128.5 | 54.3 | 48.8 | 0.266 | 127.5 | 0.9997 | 2.5 |
| 125.0 | 127.5 | 53.2 | 88.3 | 0.125 | 123.6 | 1.0000 | −1.4 |
| 125.0 | 123.6 | 53.2 | 10.0 | 0.403 | 123.6 | 1.0000 | −1.4 |
| 125.0 | 123.6 | 53.2 | 47.9 | 0.269 | 123.6 | 1.0000 | −1.4 |
| 125.0 | 123.6 | 53.2 | 85.7 | 0.134 | 123.5 | 1.0000 | −1.5 |
| 127.5 | 123.5 | 53.9 | 10.0 | 0.413 | 121.7 | 0.9998 | −5.8 |
| 90.0 | 121.7 | 54.7 | 47.8 | 0.278 | 122.5 | 0.9999 | 32.5 |
| 90.0 | 122.5 | 45.8 | 85.1 | 0.030 | 94.7 | 0.9852 | 4.7 |
| 90.0 | 94.7 | 53.2 | 10.0 | 0.560 | 88.6 | 0.9995 | −1.4 |
| 90.0 | 88.6 | 54.3 | 38.2 | 0.370 | 89.6 | 0.9998 | −0.4 |
| 90.0 | 89.6 | 55.3 | 64.4 | 0.186 | 91.6 | 0.9999 | 1.6 |
| 90.0 | 91.6 | 10.0 | 91.0 | 0.000 | | | |
| 90.0 | 91.6 | 55.3 | 10.0 | 0.570 | 90.7 | 1.0000 | 0.7 |
| 90.0 | 90.7 | 55.3 | 37.2 | 0.378 | 90.7 | 1.0000 | 0.7 |
| 90.0 | 90.7 | 55.3 | 64.1 | 0.188 | 90.7 | 1.0000 | 0.7 |
| 90.0 | 90.7 | 55.3 | 10.0 | 0.570 | 90.7 | 1.0000 | 0.7 |
| 91.8 | 90.7 | 55.3 | 36.9 | 0.380 | 90.7 | 1.0000 | −1.1 |
| 93.6 | 90.7 | 54.6 | 63.8 | 0.183 | 89.4 | 0.9999 | −4.2 |
| 95.5 | 89.4 | 54.6 | 10.0 | 0.530 | 93.4 | 0.9971 | −2.1 |
| 97.4 | 93.4 | 53.8 | 36.5 | 0.366 | 92.5 | 0.9998 | −4.9 |
| 99.4 | 92.5 | 55.7 | 64.3 | 0.199 | 96.6 | 1.0000 | −2.8 |
| 101.4 | 96.6 | 56.2 | 91.8 | 0.047 | 99.6 | 0.9997 | −1.8 |
| 103.4 | 99.6 | 54.1 | 10.0 | 0.483 | 101.1 | 0.9999 | −2.3 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the methods without departing from the scope of the invention, it is intended that

What is claimed is:

1. A method for quantification of a target analyte concentration in a process solution comprising:
   (a) inputting a low estimated target analyte concentration, a high estimated target analyte concentration, and a maximum integer value for a data counter,
   (b) setting the data counter to 1,
   (c) calculating a first target analyte concentration by dividing the sum of the low estimated target analyte concentration and the high estimated target analyte concentration by 2,
   (d) calculating a first target analyte flow rate based on the first target analyte concentration and introducing a titrant at the first target analyte flow rate,
   (e) measuring a first target analyte signal value that correlates to an actual target analyte concentration,
   (f) comparing the first target analyte signal value to a threshold target analyte signal value and a maximum target analyte signal value, and if the first target analyte signal value is between the threshold target analyte signal value and the maximum target analyte signal value, entering the first target analyte concentration and the first target analyte signal value as a first data pair into a data array,
   (g) if the first data pair is entered into the data array, then increasing the data counter by 1, or if the first data pair is not entered into the data array, repeating steps (c) to (f) with the data counter at the same value,
   (h) calculating a next target analyte concentration using the equation:

$$C_{l+1} = C_l + \frac{C_{max} - C_{min}}{n} \quad (1)$$

where n is the maximum integer value for the data counter, $C_{l+1}$ is the next target analyte concentration, $C_l$ is a previous target analyte concentration, $C_{max}$ is the high estimated target analyte concentration or a concentration calculated from equation 3 and $C_{min}$ is the low estimated target analyte concentration or a concentration calculated from equation 4, wherein if the next target analyte concentration, $C_{l+1}$, is greater than $C_{max}$, then $C_{l+1}$ is set to equal $C_{min}$,
   (i) calculating a next target analyte flow rate based on the next target analyte concentration and introducing a titrant at the next target analyte flow rate,
   (j) measuring a next target analyte signal value that correlates to the actual target analyte concentration,
   (k) comparing the next target analyte signal value to a threshold target analyte signal value and a maximum target analyte signal value, and if the next target analyte signal value is between the threshold target analyte signal value and the maximum target analyte signal value, entering the next target analyte concentration and the next target analyte signal value as a next data pair into the data array,
   (l) if the next data pair is entered into the data array, then increasing the data counter by 1, or if the next data pair is not entered into the data array, repeating steps (i) to (k) with the data counter set to the same value,
   (m) repeating steps (h)-(l) until the number of data pairs entered into the data array equals the maximum value for the data counter,
   (n) calculating $\Sigma x$, $\Sigma x^2$, $\Sigma y$, $\Sigma y^2$, and $\Sigma xy$ wherein x is the target analyte concentration and y is the signal value for each data pair,
   (o) calculating SXX, SYY, and SXY using the following equations:

$$SXX = \Sigma x^2 - \frac{(\Sigma x)^2}{n}, \quad (2a)$$

$$SYY = \Sigma y^2 - \frac{(\Sigma y)^2}{n}, \quad (2b)$$

and $$SXY = \Sigma xy + \frac{(\Sigma x)(\Sigma y)}{n}, \quad (2c)$$

(p) calculating an endpoint concentration at (i) a minimum target analyte signal value when the target analyte concentration is inversely proportional to the target analyte signal value or (ii) a maximum target analyte signal value when the target analyte concentration is directly proportional to the target analyte signal value using the following equation:

$$C_{max} = \frac{\Sigma x}{n} - \left(\frac{SXX}{SXY}\right) \cdot \left(\frac{\Sigma y}{n}\right) \quad (3)$$

(q) calculating a minimum concentration at (i) a maximum target analyte signal value when the target analyte concentration is inversely proportional to the target analyte signal value or (ii) a minimum target analyte signal value when the target analyte concentration is directly proportional to the target analyte signal value using the following equation:

$$C_{min} = \left(\frac{SXX}{SXY}\right) \cdot \left(A_m - \frac{\Sigma y}{n} + \left(\frac{SXY}{SXX}\right) \cdot \frac{\Sigma x}{n}\right), \quad (4)$$

wherein $A_m$ is the target analyte signal value,
   (r) repeating steps (h)-(l) and reassigning data pair designations so the first data pair entered is the first data pair replaced,
   (s) repeating steps (n)-(r) until the reaction endpoint is reached or the process is stopped.

2. The method of claim 1 wherein target analyte signal values are absorbance values, fluorescence values, conductance values, redox potential values, turbidity values, or electrochemical values.

3. The method of claim 1 wherein maximum integer value for the data counter is 3.

4. The method of claim 3 wherein maximum integer value for the data counter is 4.

5. The method of claim 3 wherein maximum integer value for the data counter is 5.

6. The method of claim 1 wherein target analyte signal values are absorbance values.

7. The method of claim 6 wherein equation 1 is:

$$C_{l+1} = C_l + \frac{C_{max} - C_{min}}{3}.$$

8. The method of claim 7 wherein equations 2a, 2b, and 2c are:

$$SXX = \Sigma x^2 - \frac{(\Sigma x)^2}{3}, \quad (2a)$$

$$SYY = \Sigma y^2 - \frac{(\Sigma y)^2}{3}, \quad (2b)$$

and $$SXY = \Sigma xy + \frac{(\Sigma x)(\Sigma y)}{3}. \quad (2c)$$

9. The method of claim 8 wherein equation 3 is:

$$C_{max} = \frac{\Sigma x}{3} - \left(\frac{SXX}{SXY}\right) \cdot \left(\frac{\Sigma y}{3}\right).$$

10. The method of claim 9 wherein equation 4 is:

$$C_{min} = \left(\frac{SXX}{SXY}\right) \cdot \left(A_m - \frac{\Sigma y}{3} + \left(\frac{SXY}{SXX}\right) \cdot \frac{\Sigma x}{3}\right).$$

11. The method of claim 10 wherein the target analyte concentration is inversely proportional to the target analyte signal value.

12. The method of claim 10 wherein the target analyte concentration is directly proportional to the target analyte signal value.

13. The method of claim 10 wherein the threshold value of absorbance of the process solution is from about 0.01 to about 0.1.

* * * * *

UNITED STATES PATENT AND TRADEMARK OFFICE
CERTIFICATE OF CORRECTION

PATENT NO. : 10,379,091 B2
APPLICATION NO. : 15/511730
DATED : August 13, 2019
INVENTOR(S) : Paul R. Kraus et al.

It is certified that error appears in the above-identified patent and that said Letters Patent is hereby corrected as shown below:

On the Title Page

Column 2, under "Other Publications", Line 4:
"Sully, B.D.," should read "Sully, B.D., et al.,"

In the Claims

On Column 22, Claim 2, Line 51:
"turbitity" should read "turbidity"

Signed and Sealed this
First Day of December, 2020

Andrei Iancu
*Director of the United States Patent and Trademark Office*